(12) United States Patent
Abramoff et al.

(10) Patent No.: US 11,786,148 B2
(45) Date of Patent: Oct. 17, 2023

(54) AUTONOMOUS DIAGNOSIS OF EAR DISEASES FROM BIOMARKER DATA

(71) Applicant: Digital Diagnostics Inc., Coralville, IA (US)

(72) Inventors: Michael D. Abramoff, University Heights, IA (US); Ryan Amelon, University Heights, IA (US)

(73) Assignee: Digital Diagnostics Inc., Coralville, IA (US)

( * ) Notice: Subject to any disclaimer, the term of this patent is extended or adjusted under 35 U.S.C. 154(b) by 996 days.

(21) Appl. No.: 16/529,685

(22) Filed: Aug. 1, 2019

(65) Prior Publication Data

US 2020/0037930 A1     Feb. 6, 2020

Related U.S. Application Data

(60) Provisional application No. 62/713,283, filed on Aug. 1, 2018.

(51) Int. Cl.
*A61B 5/12* (2006.01)
*A61B 5/00* (2006.01)
(Continued)

(52) U.S. Cl.
CPC ............ *A61B 5/121* (2013.01); *A61B 5/0066* (2013.01); *A61B 5/4842* (2013.01);
(Continued)

(58) Field of Classification Search
CPC ................................................. G06Q 50/20–26
See application file for complete search history.

(56) References Cited

U.S. PATENT DOCUMENTS 10,115,194 B2   10/2018  Niemeijer et al.
2007/0134814 A1*  6/2007  Kajander ........... G01N 33/6893
                                                    436/524
(Continued)

FOREIGN PATENT DOCUMENTS

WO    WO 2018/085687 A1    5/2018

OTHER PUBLICATIONS

IBM, "Recurrent Neural Networks" IBM Cloud Education (Year: 2020).*

(Continued)

*Primary Examiner* — Neal Sereboff
(74) *Attorney, Agent, or Firm* — Fenwick & West LLP

(57) ABSTRACT

A fully autonomous system is used to diagnose an ear infection in a patient. For example, a processor receives patient data about a patient, the patient data comprising at least one of: patient history from medical records for the patient, one or more vitals measurements of the patient, and answers from the patient about the patient's condition. The processor receives a set of biomarker features extracted from measurement data taken from an ear of the patient. The processor synthesizes the patient data and the biomarker features into input data, and applies the synthesized input data to a trained diagnostic model, the diagnostic model comprising a machine learning model configured to output a probability-based diagnosis of an ear infection from the synthesized input data. The processor outputs the determined diagnosis from the diagnostic model. A service may then determine a therapy for the patient based on the determined diagnosis.

23 Claims, 5 Drawing Sheets

(51) Int. Cl.
*G16H 10/60* (2018.01)
*G16H 50/20* (2018.01)
*G16H 50/30* (2018.01)
*G16H 50/70* (2018.01)
*A61B 1/227* (2006.01)

(52) U.S. Cl.
CPC ........... *A61B 5/7275* (2013.01); *G16H 10/60* (2018.01); *G16H 50/20* (2018.01); *G16H 50/30* (2018.01); *G16H 50/70* (2018.01); *A61B 1/227* (2013.01)

(56) References Cited

U.S. PATENT DOCUMENTS

| | | | |
|---|---|---|---|
| 2009/0185191 | A1 | 7/2009 | Boppart et al. |
| 2015/0065803 | A1* | 3/2015 | Douglas ............... G06T 7/143 600/200 |
| 2016/0055307 | A1 | 2/2016 | Macoviak et al. |
| 2016/0140300 | A1 | 5/2016 | Purdie et al. |
| 2016/0262627 | A1* | 9/2016 | Hecker ................... A61B 5/08 |
| 2016/0292856 | A1* | 10/2016 | Niemeijer ............. G06V 10/82 |
| 2017/0323064 | A1 | 11/2017 | Bates |
| 2018/0064374 | A1* | 3/2018 | Givens .................. G16H 40/63 |
| 2020/0268260 | A1* | 8/2020 | Tran ...................... A61B 5/1118 |

OTHER PUBLICATIONS

Bhavana et al., "Smartphone Otoscopy Sans Attachment: A Paradigm Shift in Diagnosing Ear Pathologies" OTO Open 1-6 The Authors 2018 (Year: 2018).*

Lycke et al. "Implementation of uHear™—an iOS-based application to screen for hearing loss—in older patients with cancer undergoing a comprehensive geriatric assessment" LyckeM, et al, Implementation of uHear™—an iOS-based application to screen for hearing loss—in older pat . . . , J Geriatr Oncol (Year: 2016).*

Chan et al., "Detecting middle ear fluid using smartphones" Chan et al., Sci. Transl. Med. 11, eaav1102 (2019) May 15, 2019 (Year: 2019).*

Janatka et al., "Examining in vivo Tympanic Membrane Mobility Using Smart Phone Video-Otoscopy and Phase-based Eulerian Video Magnification" Medical Imaging 2017: Computer-Aided Diagnosis, edited by Samuel G. Armato III, Nicholas A. Petrick, Proc. of SPIE vol. 10134, 101341Y • (Year: 2017).*

PCT International Search Report and Written Opinion, PCT Application No. PCT/US2019/044758, dated Oct. 4, 2019, 18 pages.

* cited by examiner

AUTONOMOUS DIAGNOSIS OF EAR DISEASES FROM BIOMARKER DATA

CROSS REFERENCE TO RELATED APPLICATIONS

This application claims the benefit of U.S. Provisional Application No. 62/713,283, filed Aug. 1, 2018, the disclosure of which is hereby incorporated by reference herein in its entirety.

BACKGROUND

This invention relates generally to autonomously assessing, diagnosing, and prescribing therapy for ear infections, such as acute otitis media (AOM). To diagnose ear infections, physicians typically utilize an otoscope, pneumatic otoscope or tympanometry as a tool. However, these techniques are not infallible and are subject to error, thus resulting in a historical over-diagnosis of ear infections. Problematically, variance in physician analysis of the results of use of otoscopy, pneumatic otoscopy or tympanometry is a cause in this historical over-diagnosis. Existing systems lack an objective tool for ensuring an accurate diagnosis and require expert physician interpretation, lacking the capability of a fully-autonomous tool to automatically diagnosis ear infections and prescribe antibiotics, which would reduce a cost burden on society caused by the over-diagnosis brought on by the existing systems.

SUMMARY

Systems and methods are described herein for using an objective service for accurately assessing, diagnosing, and prescribing therapy for ear infections. In an embodiment, a machine learning model generates an output of a probability-based diagnosis based on inputs including biomarker features and patient history. The received biomarker features may include overlapping and/or non-overlapping biomarker feature features. For example, the biomarker features may be image biomarkers that indicate one or more anatomical features found in an image of an ear, as well as a location at which the one or more anatomical elements are present in the ear. The biomarker features may also include acoustic biomarkers that are derived from responses of an ear to a pressure stimulus. The probability-based diagnosis may indicate a diagnosis along with a probability that the diagnosis is correct, which may be used, in conjunction with rules or probability-based models, to output a definitive diagnosis to a user (e.g., a doctor or other health care professional, or to the patient).

In an embodiment, a processor receives patient data about a patient, where the patient data includes patient history from medical records for the patient, one or more vitals measurements of the patient, and/or answers from the patient about the patient's condition. As used herein, answers from the patient may be obtained directly from the patient or indirectly, e.g., from the patient's proxy. The patient's condition may include a present condition and/or a medical history of the patient, including a history of the present illness for the patient. The processor receives a set of biomarker features extracted from measurement data taken from one or more ears of the patient. The processor synthesizes the patient data and the biomarker features into input data, and applies the synthesized input data to a trained diagnostic model. In some embodiments, the diagnostic model comprises a machine learning model configured to output a probability-based diagnosis of an ear infection from the synthesized input data. The processor then outputs the determined diagnosis from the diagnostic model. A service (e.g., a clinical decision support system) may then determine a therapy for the patient based on the determined diagnosis, for example, using an expert system that applies a set of rules for determining the therapy.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Overview

Figure 1:
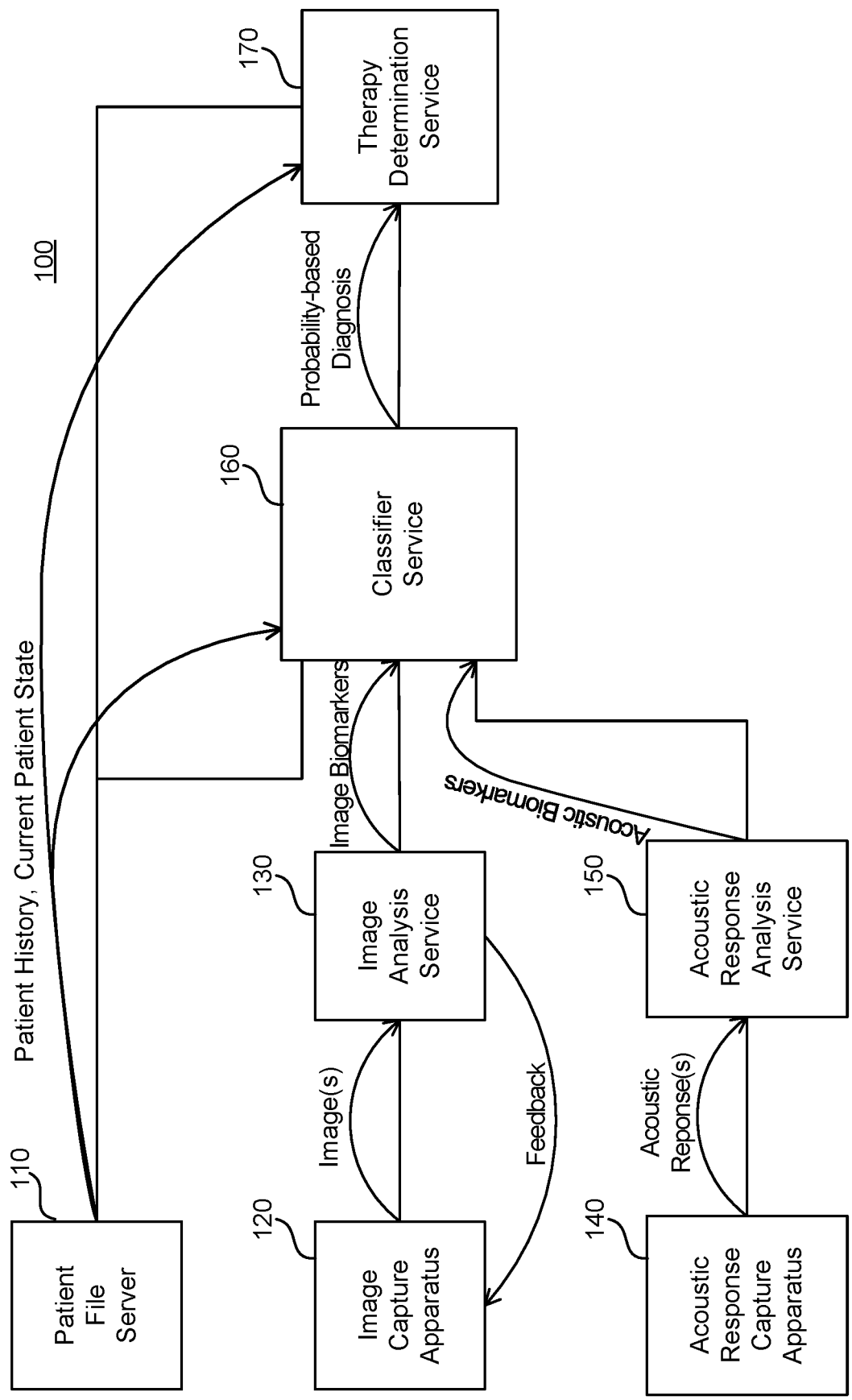
FIG. 1 is an illustrative block diagram of components used in a system for autonomously diagnosing an ear disease and generating a therapy therefor, and includes an illustrative flow of data through the system.

FIG. 1 is an illustrative block diagram of components used in a system for autonomously diagnosing an ear disease and generating a therapy therefor, and includes an illustrative flow of data through the system. FIG. 1 depicts system 100, which includes patient file server 110, image capture analysis 120, image analysis service 130, acoustic response capture apparatus 140, acoustic response analysis service 150, classifier service 160, and therapy determination service 170. While depicted as separate components of system 100, some or all of image analysis service 130, acoustic response service 150, classifier service 160, and therapy determination service 170, may be consolidated into one server or apparatus. For example, such a consolidated apparatus may be a hardware module and/or software module used by individual doctors for assistance in diagnosing ear disease, such as AOM. Further, each depicted service may be implemented in one or more servers, or may be instantiated at a client site (e.g., a doctor's office) where a client (e.g., doctor) subscribes to the service. Alternatively, the service may be implemented on a client device (e.g., a patient's mobile device) in communication with one or more servers.

Patient file server 110 may include a database that stores electronic files of patients. The term patient, as referred to herein, may be any human being, such as a child, adolescent, or adult. The electronic files of each patient may indicate the long-term history of the patient. The term long-term history, as used herein, refers to historical data gathered by one or more doctors, clinicians (e.g., doctor's assistants, nurses, etc.), or input by the patient himself or herself, or proxy such as parent or guardian. The historical data includes health data. Health data may include temperature data. (e.g., last measured temperature along with a time and date at which the temperature was taken, or several patient temperatures each with their respective times and dates). Temperature data may be accompanied by the technique by which the temperature was measured (e.g., oral, anal, forehead, device). The health data may also include any other parameters corresponding to the patient, such as history of present illness, blood pressure, age, gender, weight, height, current prescriptions, pain severity assessment (e.g., on a scale from 1 to 10), duration of symptoms, allergies, frequency of ear issues, and the like. Each piece of historical data may be accompanied by time and/or date information.

In an embodiment, when current patient state is received by an operator during a visit by a patient, the current patient state may be documented, but be immediately sent to an electronic patient file. The term operator, as used herein, is likely not to be a medically-trained person, but may be a clinician. The systems and methods described herein, for example, may result in a therapy determination without a need to consult a clinician. The term current patient state, as used herein, refers to health data of a patient that is current as to a time at which a diagnosis is taken. For example, if a patient visits a doctor's office on Jul. 24, 2019 at 5:00 pm, the current patient state may include temperature, height, and weight data of the patient on Jul. 24, 2019 at, or around, 5:00 pm. Where the current patient state is immediately sent to the electronic patient file, the electronic patient file is complete. However, for example where the current patient state is not immediately sent to the electronic file or the electronic patient file is otherwise incomplete, and an operator may, in having classifier service 160 output a diagnosis, separately transmit or input the current patient state to classifier service 160. For example, the operator may input into a user interface of an application corresponding to classifier 160 the current patient state. The therapy determination service 170 may also prompt the operator and/or the patient with questions that are used to determine the current patient state.

Image capture apparatus 120 may be any apparatus used to capture an image of a patient's ear (e.g., the inner ear of the patient). Image capture apparatus 120 may, for example, be an otoscope. Image capture apparatus 120 may perform visible light imaging. Image capture apparatus 120 may perform optical coherence tomography (OCT) imaging. In an embodiment, image capture apparatus 120 captures an image of the eardrum and/or adjacent structures to the eardrum. Image capture apparatus 120 may have snapshot OCT capability and/or continuous A-scan capability (e.g., where focus of image capture apparatus 120 is continuously adjusted as different images (e.g., OCT images) are taken). Image capture apparatus 120 may have a plurality of different center wavelengths for OCT imaging. Image capture apparatus 120 may be capable of producing two-dimensional (2D) and/or three-dimensional (3D) images, along with timestamps of when those images were taken.

Image capture apparatus 120 may navigate to a field of view including predetermined anatomical structures, such as an ear drum. The navigation may be performed automatically based on instructions from a processor, or may be performed manually by a user, such as a doctor doctor's assistant, or an untrained user. In an embodiment, image capture apparatus 120 includes, or is operably coupled to, a display. The display may indicate feedback from image analysis service 130, and may indicate an enlarged view of images captured by a camera sensor of image capture apparatus 120 of the inside of an ear.

Image analysis service 130 receives images from image capture apparatus 120 and processes the images. Where the images are sufficient for identifying image biomarkers, image analysis service 130 extracts the image biomarkers and transmits the image biomarkers to classifier service 160. Where the images are not sufficient for identifying image biomarkers, feedback is provided to at least one of image capture apparatus 120 and an operator of image capture apparatus 120. Determination of whether images are sufficient for identifying image biomarkers, extraction of image biomarkers, and provision of feedback is described in further detail below with respect to FIG. 2. The term image biomarker, as used herein, refers to a data structure that indicates an anatomical feature (e.g., a blood vessel, a fissure, etc.) found in an image or a characteristic disease feature (e.g., otalgia, magnitude of tympanic membrane bulging). The biomarkers may also include, for example, the severity of drum hyperemia, the presence of effusion behind an eardrum, and/or the reflectivity of the effusion at a plurality of central wavelengths, and/or an amount of convexity or concavity of an eardrum. The image biomarker data structure may include additional information, such as a location in the image in which the anatomical feature was found, a location in the ear corresponding to where the anatomical feature sits, a confidence value indicating a probability that the anatomical feature actually is what was identified, and the like. In an embodiment, instead of or in addition to indicating the probability, the image biomarker data structure includes a determined presence of a known abnormality that may interfere with disease assessment, such as debris, imaging artifacts (e.g., reflections, shadow, motion), implants, etc. In an embodiment, image analysis service performs a sufficiency analysis in real time, or in substantially real time, to continuously provide feedback to the operator to aid in image acquisition.

Acoustic response capture apparatus 140 captures an acoustic response of an ear of a patient to one or more stimuli and transmits the acoustic response to acoustic response analysis service 150. Acoustic response capture apparatus 140 may be any device that applies pressure to an anatomical feature of a patient's ear (e.g., an eardrum). For example, acoustic response capture apparatus 140 may be a device that performs pneumatic otoscopy or tympanometry. In an embodiment, acoustic response capture apparatus 140 captures an acoustic response from standard tympanometry. In standard tympanometry, the ear canal is pressurized by acoustic response capture apparatus with air over a spectrum of pressures while sound waves at a specific frequency are transmitted to the ear. The based on the pressurization, data is received that, if graphed, plots ear pressure against at least one of absorbed sound and compliance of the eardrum. The data, or graphs of the data, are compared to template data, to determine which of a plurality of templates the data or graphs match. For example, data may be determined to match a normal response, a response indicating that fluid is present, a response indicating negative pressure exists in the middle ear, and the like.

In an embodiment, acoustic response capture apparatus 140 captures an acoustic response from wideband tympanometry. Wideband tympanometry works in a similar manner to standard tympanometry, except that, while standard tympanometry typically uses one or a small number of frequencies, wideband tympanometry uses a large number of frequencies (e.g., over 100 frequencies). Because different materials absorb different frequencies, wideband tympanometry may provide more robust data than standard tympanometry. For example, wideband tympanometry may be used to, beyond detecting middle ear fluid (due to data matching a middle ear fluid template), also detect a makeup of the fluid (e.g., whether the fluid is or is not infected). The data output by acoustic response capture apparatus 140 when using wideband tympanometry can be fed into apparatus 150 which may use machine learning models to quantify the presence of acoustic biomarkers for input to apparatus 160.

Other forms of tympanometry may be used as well by acoustic response capture apparatus 140, such as wideband tympanometry at ambient pressure, where wideband tympanometry is used at many frequencies, but only at ambient pressure, thus alleviating the need to pressurize the ear canal. The data output by acoustic response capture apparatus 140 when using wideband tympanometry can be fed into apparatus 150 which may use machine learning models to quantify the presence of acoustic biomarkers for input to apparatus 160.

Acoustic response analysis service 150 receives acoustic responses from acoustic response capture apparatus 140 and extracts acoustic biomarkers from the acoustic responses. The term acoustic biomarkers, as used herein, refers to output from a machine learning model that may be used to classify a disease. For example, the data and/or graphs output by acoustic response capture apparatus may be input into a machine learning model. The output may be indicia including the presence or amount of fluid, the classification of mucoid versus serous fluid, the type of tympanometry classification (e.g., normal, fluid present, negative pressure in middle ear, etc.), a prediction of the presence of disease itself, and/or the detection of the presence of an obstruction in the ear. Any or all of these outputs may form acoustic biomarkers. In an embodiment, the acoustic responses themselves may be used as acoustic biomarkers, without input through a machine learning model to extract biomarkers, where a model at classifier service 160 directly translates these acoustic biomarkers into a disease classification. Acoustic biomarkers and image biomarkers may be collectively referred to herein as biomarkers. Further details of acoustic response analysis service 150 are described in further detail below with respect to FIG. 3.

Classifier service 160 receives patient history from patient file server 110. Classifier service 160 also receives image biomarkers from image analysis service 130 and/or acoustic biomarkers from acoustic response analysis service 150. While FIG. 1 depicts receipt of both image biomarkers and acoustic biomarkers, in an embodiment, only one or the other of image biomarkers and acoustic biomarkers is received by classifier service 160. Classifier service 160 may also receive current patient state data. While FIG. 1 depicts classifier service 160 as receiving current patient state data from patient file server 110, classifier service 160 may receive the current patient state data from another source, such as direct input from a doctor or doctor's assistant, from the patient himself or herself, or from the operator.

Classifier service 160 synthesizes the received data and feeds the synthesized data as input into a machine learning model. The machine learning model outputs a probability-based diagnosis, which classifier service 160 transmits to therapy determination service 170. The term probability-based diagnosis refers to a diagnosis as well as a probability that the diagnosis is accurate. For example, the diagnosis may be a probability that a patient does, or does not, have AOM. In an embodiment, a diagnosis is sent without a corresponding probability that the diagnosis is accurate. Further details of classifier 160 are described in further detail below with respect to FIG. 4.

Therapy determination service 170 receives the probability-based diagnosis and generates a therapy for the patient. The therapy determination service 170 takes as input the disease diagnosis from apparatus 160 as well as patient information from apparatus 110. Service 170 may be a Clinical Decision Support System, and may be implemented as a rule-based system or as a machine learning system. As an example, the therapy decision may be to prescribe a prescription drug, such as an antibiotic. The therapy may alternatively be watchful observation with follow-up, or referral to a specialist. Therapy determination service 170, and therapy determination generally, is described in further detail below with respect to FIG. 5.

Figure 2:
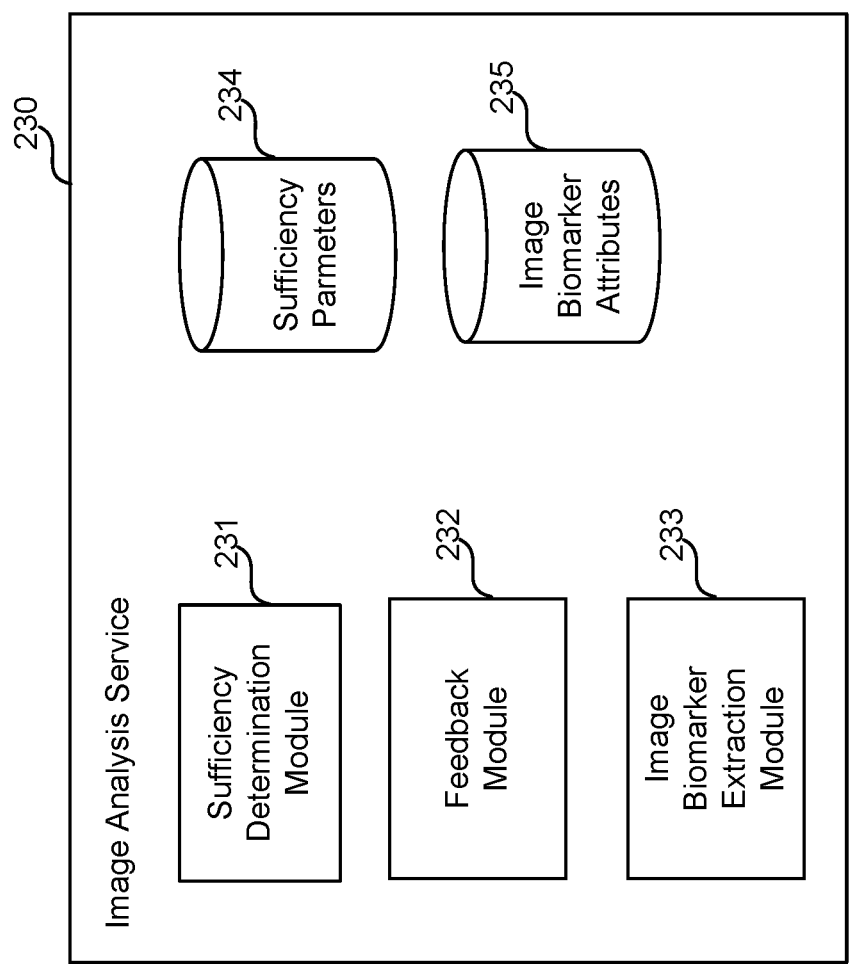
FIG. 2 is an illustrative diagram of modules of an image analysis service used to produce image biomarkers used in the diagnosis of an ear disease.

FIG. 2 is an illustrative diagram of modules of an image analysis service used to produce image biomarkers used in the diagnosis of an ear disease. Image analysis service 230 is depicted as including sufficiency determination module 231, feedback module 232, image biomarker extraction module 233, sufficiency parameters database 234, and image biomarker attributes database 235. The modules depicted in FIG. 2 may be executed by a processor of a server or device hosting image analysis service 230. The execution of the modules may be driven by computer-readable instructions on a non-transitory computer-readable medium that, when executed, cause the processor to perform the operations described with respect to FIG. 2. The databases depicted in FIG. 2 may be local to a device or server hosting image analysis service 230, or may be remote to such a device or server, and accessible by way of a network, such as a local area network or the Internet. The sufficiency parameters database 234 and image biomarker attributes database 235 may be the learned weights of a machine learning model used to calculate outputs of the image analysis service 130.

Sufficiency determination module 231 determines whether an image received from image capture apparatus 120 is sufficient for extraction of image biomarkers. Sufficiency determination may be based quality (such as the input image/signal quality) or protocol (such as whether required anatomical landmarks are present in the image). Sufficiency determination module 231 may determine sufficiency of an image based on parameters defined in sufficiency parameters database 234. For example, sufficiency parameters database 234 may include image quality parameters or the learned weights of one or more machine learning models used to calculate image quality. The quality parameters may be based on resolution, a lack of debris in the photograph, or the learned weights of a machine learning model.

The quality parameters may be driven by a deep learning network that, from a training set, models aspects of an image or a transformed image, that are of sufficient quality, and measures received images against an output of the model. For example, the model may be trained to determine whether an image includes a correct field of view, whether the image has a background that is set to a constant value, whether the image is down-sampled, etc. Using the model, or other quality parameters indicated by sufficiency parameters database 234, sufficiency determination module 231 determines whether received images are of sufficient quality. In an embodiment where multiple images are input to image analysis service 130 by way of a video captured by image capture apparatus 120, sufficiency determination module 231 may use an RNN (recurrent neural network) model for video frame selection for image quality. Because the data is being processed on a continuous basis, the RNN may be used to select a plurality of consecutive sufficient frames to avoid being overburdened with processing all frames of the video, where the consecutive sufficient frames are, alone, sufficient for image analysis. Machine learning models, as described herein, may be any form of machine model, such as convolutional neural networks (CNNs), RNNs, and the like.

Sufficiency parameters database 234 may also include image adherence parameters. For example, sufficiency parameters database 234 may include entries describing various landmarks and required positions of those landmarks within a viewing frame. For instance, an entry may indicate that a tympanic membrane must be within a field of view. Sufficiency determination module 231 may process an image to determine whether the image protocol adherence requirements in sufficiency parameters database 234 are met when determining whether the image is sufficient for extraction of image biomarkers. As an example, sufficiency determination module 231 may obtain a set of samples of a portion of an image, where each sample corresponds to a location in the ear (e.g., ear canal, tympanic membrane, malleus, umbo, light reflex, etc.). The samples may be applied by sufficiency determination module 231 to a trained feature detection model (which may also be stored in sufficiency parameters database 234), the model comprising a neural network that is configured to output a likelihood of whether the sample contains an ear object. Sufficiency determination module 231 may determine, from the output, whether the image sufficiently adheres to the image adherence parameters.

Where an image is determined to be insufficient for extraction of image biomarkers, feedback module 232 transmits feedback to image capture apparatus 120. In an embodiment where image capture apparatus 120 has a display, feedback module 232 transmits to image capture apparatus 120 an indication, for inclusion on the display, of why an image is insufficient. For example, if the quality is a problem, a color scale (e.g., red, yellow, green) may indicate the degree to which the quality was insufficient. If image adherence is a problem, feedback module 232 may transmit instructions (e.g., an arrow on the display) to move the view of the image capture apparatus 120 to one side or the other. Feedback module 232 may cause the display to circle an area of an image that needs to be centered, and may instruct the operator to center that portion of the image.

Feedback module 232 may transmit any sort of instruction for moving a field of view of a camera sensor in any direction, such as forward or backward (to improve depth of view), left, right, up, down, or diagonally (to improve the centering of an anatomical feature or structure), etc. These instructions may be displayed on a display, may be output through a speaker, may be printed to text, etc. In an embodiment, image capture apparatus 120 may receive instructions from image analysis service 130 to automatically adjust the position of a camera sensor in the same manners described above with respect to manual movement. In an embodiment, image capture apparatus 120 may receive a command to output, on the display, a notification that sufficient quality images have received, and thus image capture may be stopped. While the term image is used herein, image capture apparatus 120 may capture video, from which individual images are derived.

In an embodiment, feedback module 232 may command image capture apparatus 120 (or a peripheral operably coupled thereto) to output auditory signals to indicate needed changes to image quality or adherence, or to indicate that. For example, image analysis service 130 may command image capture apparatus 120 to beep or otherwise sound when sufficient quality imaging has been received, and thus imaging can be stopped. Similarly, feedback module 232 may command image capture apparatus 120 (or a peripheral operably coupled thereto) to generate haptic output to alert an operator to any alert or notification described herein (e.g., a vibration to indicate that sufficient exam has been acquired and thus further imaging is no longer needed).

Feedback module 232 may use any mechanism described above to direct the operator to an optimal imaging location (e.g., in the external meatus). The optimal imaging location may be with respect to anatomical features, location of debris, pathology of the eardrum, and the like, as determined, e.g., by a machine learning model. In an embodiment, feedback module 232 may instruct the operator to clean the device or clear debris (e.g., cerumen) near an imaging location.

Image biomarker extraction module 233 extracts image biomarkers from the images received from image capture apparatus 120. Image biomarkers include the detection of relevant anatomy and disease/pathological features associated with the diagnosis. Image biomarker extraction module 233 may determine what attributes of an image form a biomarker based on entries of image biomarker attributes database 235. Image biomarker attributes database 235 includes entries that indicate patterns associated with anatomical features, such as fissure patterns, bulging patterns, darkening and lightening patterns relative to a background, and the like. Image biomarker attributes database 235 may include one or more trained machine models that may be used by image biomarker extraction module to input an image through, and receive as output a determination of biomarkers. Image biomarker extraction module 232 extracts, from the image, the location of the biomarker (e.g., with reference to an anatomical structure, such as a tympanic membrane or eardrum). The location may be indicated in terms of coordinates that may be normalized relative to an anatomical structure. Image biomarker extraction module 232 includes, in the image biomarker, the location, as well as an indication of what the biomarker is (e.g., a fissure). In an embodiment, image biomarker extraction module 233 may also include a confidence value, or probability, that the biomarker actually is what the image biomarker indicates it is (e.g., an 80% confidence that this is a fissure). Image analysis service 230 transmits the image biomarker to classifier service 160.

Further details of how to detect anatomical features in images and extract biomarkers from images are described (using terms relating to extracting "features") in U.S. Pat. No. 10,115,194, issued Oct. 30, 2018, the disclosure of which is hereby incorporated by reference herein in its entirety.

Figure 3:
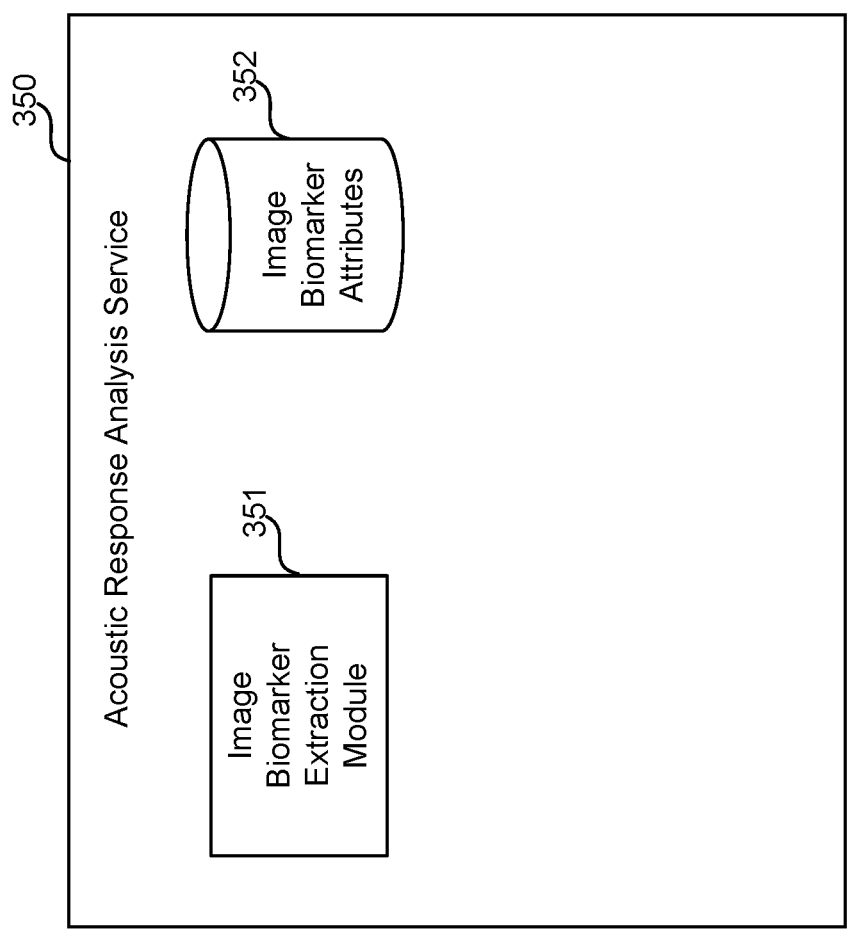
FIG. 3 is an illustrative diagram of an acoustic response analysis service used to produce acoustic biomarkers used in the diagnosis of an ear disease.

FIG. 3 is an illustrative diagram of an acoustic response analysis service used to produce acoustic biomarkers used in the diagnosis of an ear disease. Acoustic response analysis service 350 includes acoustic biomarker extraction module 351 and acoustic biomarker attributes database 352. The modules depicted in FIG. 3 may be executed by a processor of a server or device hosting acoustic response analysis service 350. The execution of the modules may be driven by computer-readable instructions on a non-transitory computer-readable medium that, when executed, cause the processor to perform the operations described with respect to FIG. 3. The databases depicted in FIG. 3 may be local to a device or server hosting acoustic response analysis service 330, or may be remote to such a device or server, and accessible by way of a network, such as a local area network or the Internet. Acoustic biomarker extraction module 351 may execute a machine learning model to translate outputs from acoustic response capture apparatus 140. The machine learning model may be retrieved from acoustic biomarker attributes database 352. Further details of biomarker extraction and use of the machine learning model are described above with respect to FIG. 1.

Figure 4:
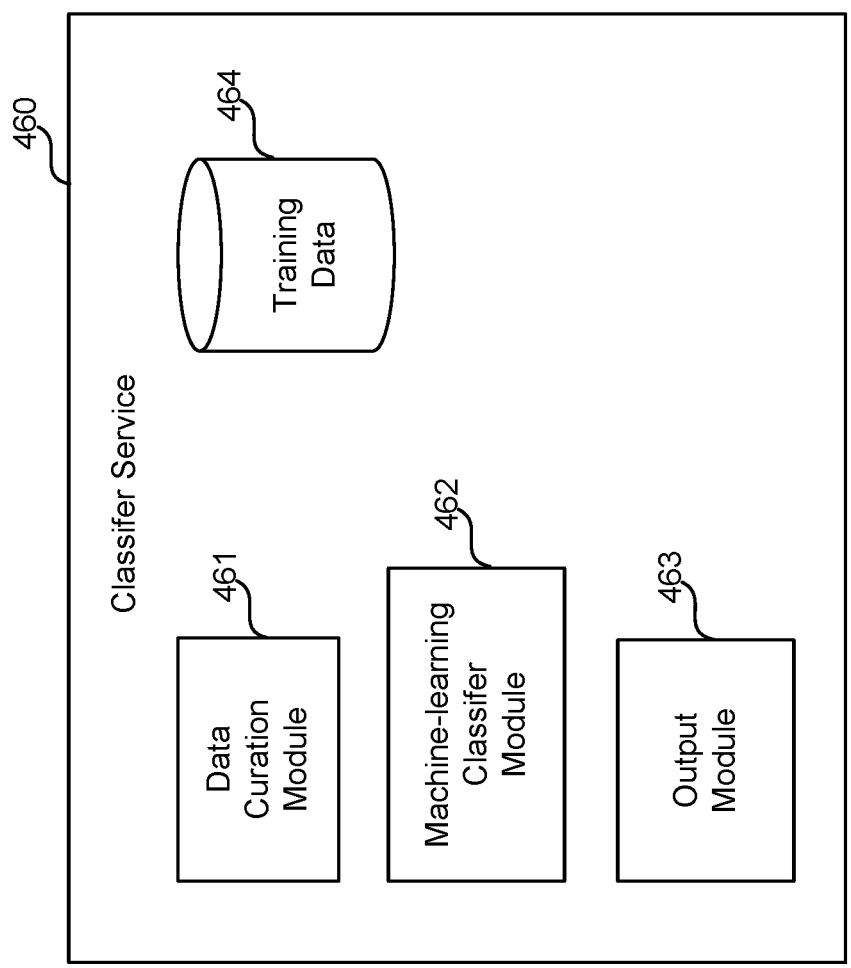
FIG. 4 is an illustrative diagram of a classifier service used to autonomously generate a probability-based diagnosis of an ear disease.

FIG. 4 is an illustrative diagram of a classifier service used to autonomously generate a probability-based diagnosis of an ear disease. Classifier service 460 includes data curation module 461, machine-learning classifier module 462, output module 463, and training data database 464. The modules depicted in FIG. 4 may be executed by a processor of a server or device hosting image analysis service 460. The execution of the modules may be driven by computer-readable instructions on a non-transitory computer-readable medium that, when executed, cause the processor to perform the operations described with respect to FIG. 4. The databases depicted in FIG. 4 may be local to a device or server hosting classifier 460, or may be remote to such a device or server, and accessible by way of a network, such as a local area network or the Internet.

Data curation module 461 collects data used as inputs by machine-learning classifier module 462 and feeds that data as an input to machine-learning classifier module 462. In an embodiment, as patient history, current patient state, image biomarkers, and/or acoustic biomarkers are received, data curation module 461 feeds this data into machine-learning classifier module 462 as input features. In another embodiment, such data is collected until a sufficient amount of data for input into machine-learning classifier module 462 is received, and then is input together to machine-learning classifier module 462.

Machine-learning classifier module 462 executes a machine learning model trained using data in training data database 464. In one embodiment, the machine learning model is a recurrent neural network (RNN) model, and training data in training data database 464 is updated on an ongoing basis (e.g., for subsequent points in time) to improve the diagnostic accuracy of the machine learning model. In an embodiment, machine-learning classifier module selects one or more machine learning models from several machine learning models to use depending on various factors. These factors may include which disease biomarker detection and/or segmentation is being evaluated, and which anatomy location/segmentation is being evaluated. For example, different anatomical structures in the ear may each have dedicated machine learning models trained using training data from those anatomical structures in training data database 464, leading to more precise outputs from the machine learning models. Similarly, different types of biomarkers (e.g., fissures versus blood flow markers) may each have dedicated machine learning models for similar reasons. Such machine learning models do not have to be (statistically) independent and may in fact be partially overlapping in their combined solution space. Where multiple machine learning models are selected by machine-learning classifier module, output form one module may form input of another module. Further discussion of machine models, such as neural networks, and selection of the best machine models from a pool of candidate machine models, is discussed in further detail in commonly owned U.S. Pat. No. 10,115,194, issued Oct. 30, 2018, the disclosure of which is hereby incorporated by reference herein in its entirety.

An example of machine-learning classifier module 462 classifying inputs may be as follows. To detect tympanic membrane bulging, image analysis service 130 may extract image regions of a relevant image and send them to machine-learning classifier module 462. Machine-learning classifier module 462 may select one or more non-orthogonal machine learning model(s) trained to detect a degree of bulging considering the region in and around the tympanic membrane. Machine-learning classifier module 462, based on the degree of bulging, classifies the image as including a particular disease. The disease may be determined based on a machine learning model as well (e.g., with training data in training data database 464). The disease may alternatively be determined based on a heuristic, or a combination of a machine learning model and a heuristic. The disease determination may include a probability that the disease determination is accurate, which may also be computed based on the machine learning model, the heuristic, or a combination of the two.

In an embodiment, synthesized data for a patient (e.g., as synthesized by data curation module 461) may be stored as a training example for a patient, the training example including the synthesized data that was used as an input into the model selected by the machine-learning classifier module 462, as well as a label that indicates whether the model determined the patient to have an ear infection. The training data, in the aggregate for several patients, may be stored to training data database 464, and may be used to train or further refine one or more diagnostic models. During training, parameters of the model may be updated to improve an objective performance threshold, which is a threshold of outputting a correct diagnostic. Training may be concluded after the objective performance threshold satisfies a condition (e.g., being sufficiently high, or reaching a mark preset by an administrator). The updated parameters for the diagnostic model may then be stored in memory of classifier service 460 for use when processing further synthesized input data.

Figure 5:
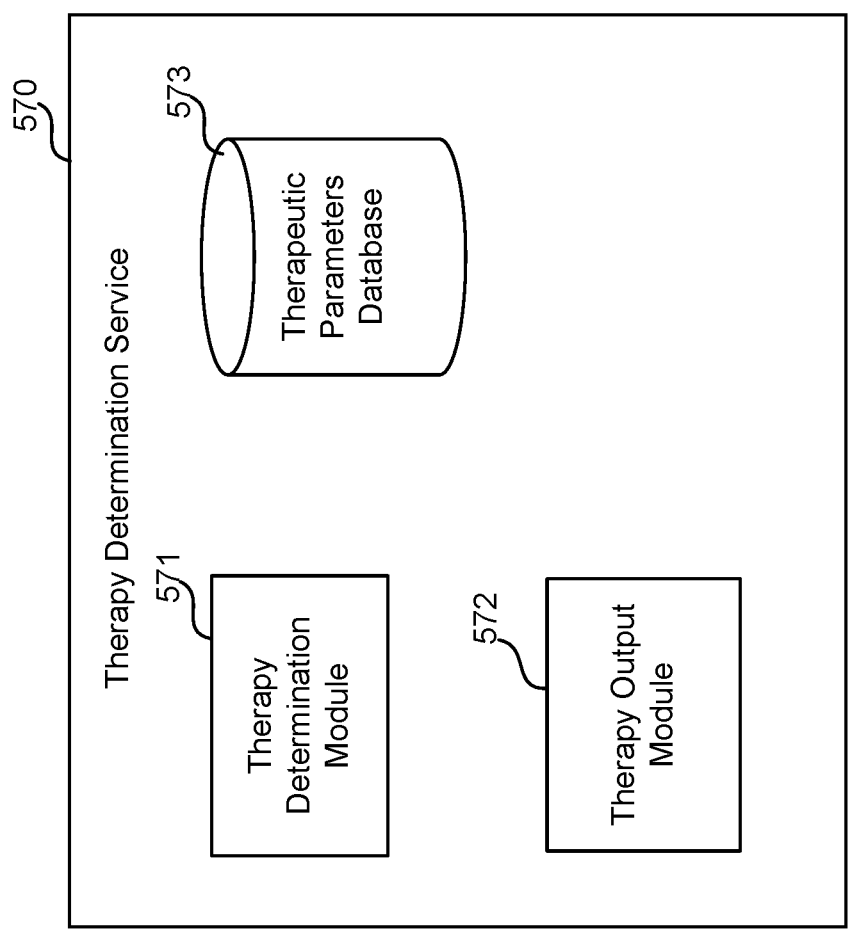
FIG. 5 is an illustrative diagram of a therapy determination service used to autonomously generate a therapy for output to a user.

FIG. 5 is an illustrative diagram of a therapy determination service used to autonomously generate a therapy for output to a user. Therapy determination service 570 includes therapy determination module 571, therapy output module 572, and therapeutic parameters database 573. The modules depicted in FIG. 5 may be executed by a processor of a server or device hosting therapy determination service 570. The execution of the modules may be driven by computer-readable instructions on a non-transitory computer-readable medium that, when executed, cause the processor to perform the operations described with respect to FIG. 5. The databases depicted in FIG. 5 may be local to a device or server hosting therapy determination service 570, or may be remote to such a device or server, and accessible by way of a network, such as a local area network or the Internet.

Therapy determination module 571 receives the probability-based diagnosis from classifier service 160, and consults a therapeutic parameters database 573 to determine a therapy to recommend to an operator. The therapeutic parameters database 573 may contain heuristics directly from clinical practice guidelines and may be subject to change depending on changes to the clinical practice guidelines. Therapeutic parameters database 573 may be automatically updated based on the service detecting an update to clinical practice guidelines, or may be updated by an administrator based on such updates. As an example, if the detected disease is severe AOM with a 100% probability of being a correct diagnosis, therapy determination module 571 may determine the appropriate therapy to be, based on entries of therapeutic parameters database 573, which may include the type and dosage of antibiotics. In one example, antibiotics are prescribed for children six months or older (e.g., as determined based on data from patient file server 110). As another example, if the detected disease is non-severe AOM with a 100% probability of being a correct diagnosis, therapy determination module 571 may determine the appropriate therapy to be antibiotics or observation for children 6-23 months old. Dosage calculations are determined based on patient weight and/or age, as dictated in the entries of therapeutic parameters database 573. In an embodiment, a therapy decision is determined on the basis of presence and/or severity of otitis media and/or the presence of otitis media with effusion, and/or the presence of serious effusion. In an embodiment, the therapeutic parameters database 573 may contain a machine learning model used to calculate the output of the therapy determination service 570 with or without heuristics.

Therapy output module 572 outputs the determined therapy to the operator and/or to the patient. The means of output may be through a display, speaker, haptic feedback, or any other means of communicating information to the operator and/or patient. The output of the therapy may be through image capture apparatus 120, or through another apparatus, such as a client device of the operator or patient (e.g., a mobile device).

SUMMARY

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for diagnosing an ear infection, the method comprising:
   accessing a diagnostic model, wherein the diagnostic model is trained using a plurality of training examples that were generated by, for each of a plurality of patients:
      receiving patient data about a patient, the patient data comprising at least one of: patient history from medical records for the patient, one or more vitals measurements of the patient, and answers from the patient about the patient's condition;
      receiving a set of biomarker features extracted from measurement data taken from an ear of the patient by:
         obtaining an image of a portion of the patient's ear; and
         extracting one or more biomarker features from the image, the extracted biomarker features including a likelihood of whether the image contains an ear image object and a location of the ear image object, wherein extracting the one or more biomarker features from the image comprises:
            obtaining a set of samples of the ear image, each sample corresponding to a location in the ear; and
            for each of the set of samples, applying the sample to a trained feature detection model, the feature detection model comprising a neural network that is configured to output a likelihood of whether the sample contains an ear image object;
      synthesizing the patient data and the biomarker features into input data; and
      storing a training example for the patient, the training example comprising the input data for the patient and a label that indicates whether the patient has an ear infection;
   wherein the diagnostic model is trained by:
      repeatedly applying given ones of the plurality of training examples to the diagnostic model and updating parameters of the diagnostic model to improve an objective performance threshold, and
      stopping the training after the objective performance threshold satisfies a condition;
   and wherein the method further comprises:
      generating new synthesized input data for a given patient using a new image of a given portion of a given ear of the given patient;

applying the new synthesized input data to the diagnostic model, the diagnostic model comprising a machine learning model configured to output a probability-based diagnosis of an ear infection from the new synthesized input data; and outputting the probability-based diagnosis from the diagnostic model.

2. The method of claim 1, wherein the new image is at least one of a two-dimensional image or a three-dimensional optical coherence tomography image.

3. The method of claim 1, wherein the given portion of the given patient's ear comprises at least one of a tympanic membrane, an anatomical structure adjacent to a tympanic membrane, an ear canal adjacent to the tympanic membrane, a malleus, an umbo, and a light reflex.

4. The method of claim 1, wherein the new image was re-taken in response to a determination that a prior image included an abnormality that would interfere with disease assessment.

5. The method of claim 1, wherein receiving the set of biomarker features comprises:
applying a pressure stimulus to inside an ear of the patient;
receiving an acoustic response from the applied pressure stimulus;
extracting acoustic biomarker features from the received acoustic response; and
synthesizing, into the input data, the acoustic biomarker features.

6. The method of claim 5, wherein the pressure stimulus is applied using at least one of pneumatic otoscopy or tympanometry.

7. The method of claim 1, wherein the image biomarker features each further indicate a confidence value that reflects a confidence that an indicated anatomical feature of the ear was accurately determined.

8. The method of claim 1, further comprising:
determining a therapy for treatment of the ear infection based on the probability-based diagnosis; and
providing a description of the therapy.

9. The method of claim 8, wherein determining the therapy comprises:
accessing a therapeutic parameters database;
identifying an entry of the therapeutic parameters database that corresponds to both the determination of whether the given patient has a disease, as well as a probability that the determination that the given patient has the disease is true; and
determining the therapy to be a therapy indicated by the entry based on the determined diagnosis.

10. The method of claim 8, wherein determining the therapy comprises:
applying a machine learning model previously trained to associate the determined diagnosis and patient data for the given patient with a therapy.

11. A computer program product for diagnosing an ear infection, the computer program product comprising a computer-readable storage medium containing computer program code for:
accessing a diagnostic model, wherein the diagnostic model is trained using a plurality of training examples that were generated by, for each of a plurality of patients:
receiving patient data about a patient, the patient data comprising at least one of: patient history from medical records for the patient, one or more vitals measurements of the patient, and answers from the patient about the patient's condition;
receiving a set of biomarker features extracted from measurement data taken from an ear of the patient by:
obtaining an image of a portion of the patient's ear; and
extracting one or more biomarker features from the image, the extracted biomarker features including a likelihood of whether the image contains an ear image object and a location of the ear image object, wherein extracting the one or more biomarker features from the image comprises:
obtaining a set of samples of the ear image, each sample corresponding to a location in the ear; and
for each of the set of samples, applying the sample to a trained feature detection model, the feature detection model comprising a neural network that is configured to output a likelihood of whether the sample contains an ear image object;
synthesizing the patient data and the biomarker features into input data; and
storing a training example for the patient, the training example comprising the input data for the patient and a label that indicates whether the patient has an ear infection;
wherein the diagnostic model is trained by:
repeatedly applying given ones of the plurality of training examples to the diagnostic model and updating parameters of the diagnostic model to improve an objective performance threshold, and
stopping the training after the objective performance threshold satisfies a condition;
and wherein the computer code is further for:
generating new synthesized input data for a given patient using a new image of a given portion of a given ear of the given patient;
applying the new synthesized input data to the diagnostic model, the diagnostic model comprising a machine learning model configured to output a probability-based diagnosis of an ear infection from the new synthesized input data; and
outputting the probability-based diagnosis from the diagnostic model.

12. The computer program product of claim 11, wherein the new image is at least one of a two-dimensional image or a three-dimensional optical coherence tomography image.

13. The computer program product of claim 11, wherein the given portion of the given patient's ear comprises at least one of a tympanic membrane, an anatomical structure adjacent to a tympanic membrane, an ear canal adjacent to the tympanic membrane, a malleus, an umbo, and a light reflex.

14. The computer program product of claim 11, wherein the new image was re-taken in response to a determination that a prior image included an abnormality that would interfere with disease assessment.

15. The computer program product of claim 11, wherein receiving the set of biomarker features comprises:
applying a pressure stimulus to inside an ear of the patient;
receiving an acoustic response from the applied pressure stimulus;
extracting acoustic biomarker features from the received acoustic response; and synthesizing, into the input data, the acoustic biomarker features.

16. The computer program product of claim 15, wherein the pressure stimulus is applied using at least one of pneumatic otoscopy or tympanometry.

17. A diagnostic product for diagnosing an ear infection, wherein the diagnostic product is stored on a non-transitory computer readable medium and is manufactured by a process comprising:
  generating a plurality of training examples by, for each of a plurality of patients:
    receiving patient data about the patient, the patient data comprising at least one of: patient history from medical records for the patient, one or more vitals measurements of the patient, and answers from the patient about the patient's condition,
    receiving a set of biomarker features extracted from measurement data taken from an ear of the patient by:
      obtaining an image of a portion of the patient's ear; and
      extracting one or more biomarker features from the image, the extracted biomarker features including a likelihood of whether the image contains an ear image object and a location of the ear image object, wherein extracting the one or more biomarker features from the image comprises:
        obtaining a set of samples of the ear image, each sample corresponding to a location in the ear; and
        for each of the set of samples, applying the sample to a trained feature detection model, the feature detection model comprising a neural network that is configured to output a likelihood of whether the sample contains an ear image object,
    synthesizing the patient data and the biomarker features into input data for the patient, and
    storing a training example for the patient, the training example comprising the input data for the patient and a label that indicates whether the patient has an ear infection;
  for a diagnostic model, the diagnostic model comprising a machine learning model that is configured to output a diagnosis of an ear infection:
    training the diagnostic model by repeatedly applying given ones of the plurality of training examples to the diagnostic model and updating parameters of the diagnostic model to improve an objective performance threshold, and
    stopping the training after the objective performance threshold satisfies a condition; and
  storing the updated parameters for the diagnostic model on the non-transitory computer readable medium.

18. The diagnostic product of claim 17, wherein the image is at least one of a two-dimensional image or a three-dimensional optical coherence tomography image.

19. The diagnostic product of claim 17, wherein the portion of the patient's ear comprises at least one of a tympanic membrane, an anatomical structure adjacent to a tympanic membrane, an ear canal adjacent to the tympanic membrane, a malleus, an umbo, and a light reflex.

20. The diagnostic product of claim 17, wherein the image was re-taken in response to a determination that a prior image included an abnormality that would interfere with disease assessment.

21. The diagnostic product of claim 17, wherein receiving the set of biomarker features comprises:
  applying a pressure stimulus to inside an ear of the patient;
  receiving an acoustic response from the applied pressure stimulus;
  extracting acoustic biomarker features from the received acoustic response of the ear to a pressure stimulus; and
  synthesizing, into the input data, the acoustic biomarker features.

22. The diagnostic product of claim 21, wherein the pressure stimulus is applied using at least one of pneumatic otoscopy or tympanometry.

23. The diagnostic product of claim 17, wherein the image biomarker features each further indicate a confidence value that reflects a confidence that an indicated anatomical feature of the ear was accurately determined.

* * * * *